(12) United States Patent
Lu (10) Patent No.: US 7,138,147 B2
(45) Date of Patent: Nov. 21, 2006

(54) ARSENIC SULFIDE COMPOUNDS AND DERIVATIVES THEREOF FOR THE TREATMENT OF MALIGNANCIES

(75) Inventor: Daopei Lu, c/o Staff Living Quarters People Hospital Beijing Medical University, 42 Beijing (CN) 100044

(73) Assignee: Daopei Lu, Beijing (CN)

( * ) Notice: Subject to any disclaimer, the term of this patent is extended or adjusted under 35 U.S.C. 154(b) by 0 days.

(21) Appl. No.: 10/635,653

(22) Filed: Aug. 7, 2003

(65) Prior Publication Data

US 2004/0028750 A1 Feb. 12, 2004

Related U.S. Application Data

(63) Continuation of application No. 09/110,366, filed on Jul. 6, 1998.

(51) Int. Cl.
*A01N 59/22* (2006.01)
*A61K 33/36* (2006.01)

(52) U.S. Cl. ..................................... 424/620
(58) Field of Classification Search ............... 424/620, 424/621
See application file for complete search history.

(56) References Cited

U.S. PATENT DOCUMENTS

| 132,275 | A | 10/1872 | Gettings |
| 232,807 | A | 10/1880 | Dennett |
| 3,700,498 | A | 10/1972 | Kanazawa et al. |
| 4,497,780 | A | 2/1985 | Barin et al. |
| 5,759,837 | A | 6/1998 | Kuhajda et al. |
| 6,720,011 | B1 | 4/2004 | Zhang |
| 6,875,451 | B1 * | 4/2005 | Ellison et al. ............... 424/623 |
| 2002/0013371 | A1 | 1/2002 | Warrell, Jr. et al. |
| 2002/0183385 | A1 * | 12/2002 | Ellison et al. ............... 514/504 |

FOREIGN PATENT DOCUMENTS

| CN | 1061908 | * | 6/1992 |
| CN | 1061908 | A | 6/1992 |
| CN | 1079391 | A | 12/1993 |
| CN | 1081104 | A | 1/1994 |
| CN | 1119113 | A | 3/1996 |
| CN | 1121807 | A | 5/1996 |
| CN | 1122700 | A | 5/1996 |
| CN | 1131037 | A | 9/1996 |
| CN | 1133725 | A | 10/1996 |
| DE | 2 539 993 | | 3/1994 |
| DE | 43 17 331 | A1 | 12/1994 |
| FR | 2 539 993 | A1 | 3/1994 |
| JP | 51-88620 | | 3/1976 |
| LV | 11667 | B | 6/1997 |
| WO | WO 94/02108 | | 2/1994 |
| WO | WO 95/01789 | | 1/1995 |
| WO | WO 95/22336 | | 8/1995 |

OTHER PUBLICATIONS

"Diarsendisulfid $As_2S_2$", Gmelin's Arsenic, $8^{th}$ Edition, 17:417-422, 1952.
Arsen (III)-Sulfid $As_2S_2$, Gmelin's Arsenic, $8^{th}$ Edition, 17:422-433, 1952.
Qi and Bi, "Method for removing $As_2O_3$ from Realgar", Chung Yao Tung Pao, 8(5):21-22, 1983.
"Letter on Historical Facts Regarding the Development of Ai Ling No. 1 and the Clinical Use of Arsenic Trioxide in the Treatment of Acute Promyelocytic Leukemia and a Study of its Mechanism," Heilongjiang Branch of the Chinese Medical Association, Mar. 27, 1998.
Wang et al., "Arsenic Trioxide and Melarsoprol Induced Programmed Cell Death in Myeloid Leukemia Cell Lines and Function in a PML and PML-PAR$\alpha$ Independent Manner," Blood, 92(5):1497-1504, 1998.
Yuan et al., Journal of Traditional Chinese Medicines, vol. 13(8), Aug. 1988.
Zhang et al., "Discussion on methods for removing As involving use of yogurt", Zhongguo Zhongyao Zaahi, 20(9): 537, 1995.
Yuan et al., "Exploring methods for purifying Realgar", Chung Yao Tung Pao, 13(8): 17-21, 1988.
Yuan et al., "Research on traditional methods for Purifying Realgar", Chung Yao Tung Pao, 13(8); 23-26, 1988.
"Realgar", Chinese Pharmacorpia (I), Guangdong Science and Technology Publishing House, China, pp. 298-299, 1995.
Lu et al., "Effective treatment of AML-M3 (APL) and their remission maintenance with Realgar: A pilot clinical laboratory study on 38 patients", Blood, 90(10 Suppl. 1, part 1), p. 416a, #1849, 1997.
Forkner et al., "Arsenic as a therapeutic agent in chronic myelogenous leukemia", Jour. A.M.A., vol. 97, No. 1, pp. 3-5, 1931.
Stephens et al., "The therapeutic effect of solution of potassium arsenite in chronic myelogenous leukemia", Ann. Intern. Assoc., vol. 9, 1488-1502, 1936.
Monfardini et al., "Survival in chronic myelogenous leukemia: influence of treatment and extent of disease at diagnosis", Cancer, 31: 492-501, 1973.

(Continued)

*Primary Examiner*—Alton Pryor
(74) *Attorney, Agent, or Firm*—Foley & Lardner LLP (57) ABSTRACT

The present invention relates to arsenic sulfide compounds. The present invention also relates to pharmaceutical compositions useful for treating cancer, such as leukemia or lymphoma, which comprises an arsenic sulfide compound. The present invention further relates to methods for treating cancer, such as leukemia or lymphoma, using an arsenic sulfide compound. Finally, the present invention relates to processes for producing arsenic disulfide ($As_4S_4$).

9 Claims, 4 Drawing Sheets

OTHER PUBLICATIONS

Cuzick et al., "Medicinal arsenic and internal malignancies", Br. J. Cancer, 45: 904-911, 1982.
Lee et al., "Induction of gene amplification by arsenic", Science, 241: 79-81, 1988.
Wang et al., "Studies on chemically preventing leukemia", Chung Hua Chung Liu Tsa Chih, 11(3);207-210, 1989.
Pershagen et al., "On the pulmonary tumorigenicity of arsenic trisulfide and calcium arsenate in hamsters", Cancer Letters, 27:99-104, 1985.
Yamamoto et al., Tumorigenicity of inorganic arsenic compounds following intratracheal instillations to the lungs of hamsters, Int. J. Cancer, 40:220-223, 1987.
Andrea et al., "The PML and PLM/RARα Domains: from autoimmunity to molecular oncology and from retinoic acid to arsenic", Experimental Cell Research 229: 253-260, 1996.
Schenk, Handbook of Preparative Inorganic Chemistry, 1: 603, G. Brauer, Ed., Academic press, New York, $2^{nd}$ Ed., 1963.
Mervis, "Ancient remedy performs new tricks", Science, vol. 273: 578, Aug. 2, 1996.
Chemical Abstract, 63-Pharmaceuticals, vol. 11, pp. 317, #111: 219272j and 111: 219276p, 1987-1991.
Lu et al., Study of Realgar in the treatment of acute promyelocytic Leukemia (APL)- a pilot clinical and laboratory study on 32 patients, China-Korea Medical Conference '97, 1997.
Dictionary of Inorganic Compounds, vol. 1, Ac-$C_{10}$, IC-000667-IC-000671.
Germolec et al., "Arsenic induces over expression of growth factors in human keratinocytes", toxicology And Applied Pharmacology, 141:308-318, 1996.
Shen et al., "Use of arsenic trioxide ($AS_2$-$O_3$) in the treatment of acute promyelocytic Leukemia (APL): II. Clinical efficacy and pharmacokinetics in relapsed patients", Blood, vol. 89, No. 9, pp. 3354-3360, May 1, 1997.
Chen et al., "In vitro studies on cellular and molecular mechanisms of arsenic trioxide ($AS_2$-$O_3$) in the treatment of acute promyelocytic Leukemia (APL): $AS_2$-$O_3$ includes $NB_4$ cell apoptosis with down regulation of Bcl-2 expression and modulation of PML-RARα/PML proteins", Blood, vol. 88, No. 3, pp. 1052-1061, Aug. 1, 1996.
Kasper et al., "Hepatic Angiosarcoma and bronchioloalveolar carcinoma induced by Fowler's solution", JAMA, vol. 252, No. 24, pp. 3407-3408, 1984.
Cutler et al., Article IV, American Journal of the Medical Sciences, pp. 74-84.
Neubauer, "Arsenic Cancer: a review", Arsenical Cancer, Arsenic Committee of the Medical Research Council pp. 192-251, 1947.
Zhu et al., "Arsenic-induced PML targeting onto nuclear bodies: implications for the treatment of acute promyelocytic leukemia", Proc. Natl. Acad. Sci., vol. 94, pp. 3978-3983, Apr. 1997.
Hutchinson, "IX. Diseases, Etc., of the skin."
"Goodman & Gilman's The pharmacological basis of therapeutics", ninth edition, McGraw-Hill, Health Professions Division, pp. 1659-1662.
Huang, Shiling; Guo, Aixia; Xiang, Yang et al. 1995, "The Linic Study of QUINGDAI Tablet for Treating Acute Promyelocytic Leukemia", China Magazine of Hematology, 16(1):26.
Xiang, Yang; Huang, Shiling; Guo, Aixia et al., 1995, "60 Cases of Treating Acute Promyelocytic Leukemia by QUINGDAI tablet," Medical Magazine of the Liberation Army, 20(3):227-229.
"Inorganic Arsenic Compounds Other than Arsine Health and Safety Guide, Health and Safety Guide No. 708", WHO, Geneva, 1992.
"Xionghuang", Chinese Pharmacopia (I), Guangdong Science and Technology Publishing House, China, pp. 298-299, 1995.
Akao et al., "Arsenic Induces Apoptosis in B-cell Leukaemic Cell Lines in Vitro: Activation of Caspases and Down-regulation of Bcl-2 Protein", British J of Hematology, 102. 1055-1060, 1998.

Arsenic, Environmental Health Criteria 18, Geneva: WHO 1981.
Chen et al., "Use of Arsenic Trioxide ($AS_2$-$O_3$) in the Treatment of Acute Promyelocytic Leukemia (APL): I. $AS_2$-$O_3$ Exerts Dose-Dependent Dual Effects on APL Cells", Blood, vol. 89, No. 9, pp. 3345-3353, 1997.
Chung et al. "Influence for Carcinoma Cell and Lymphatic cell of Acetyl Arsonate", Yakhak Hoeji vol. 40, No. 5, pp. 599-607, 1996.
de Thè, "L'oyxyde d'arsenic: après l'acide rètinoique, un nouvea traitement ciblède la leucèmie aiguëpromyèlocytaire", mèdecine/ science; 13:867-71, 1997.
Flamigni et al., "Effect of Sodium Arsenite on the Induction and Turnover of Ornithine Decarboxylase Activity ub Erythroleukemia Cells", Cell Biochemistry and Function, vol. 7:213-217, 1989.
Fluke 1995/96 Catalog, p. 152-153, Jul. 1995.
Ishinish N. et al., "Study on Chronic Toxicity of Arsenic Trioxide in Rats with a Special Reference to the Liver Damages", Fukuok Acta Medicine, 71:27, 1980.
König et al., "Comparative Activity of Melarsoprol and Arsenic trioxide in Chronic B—Cell Leukemia Lines", Blood, vol. 90, No. 2, pp. 562-570, Jul. 15, 1997.
Kwong et al., Delicious Poison: Arsenic Trioxide for the treatment of Leukemia, Blood 89-3487-B, May 1997.
Li et al., "Traditional Chinese and Western Medicine in the treatment of 27 Patients with Malignant Lymphoma", Chinese J Oncology, 10:61-62, 1988.
Pories et al., "Trace Elements that Act to Inhibit Neoplastic growth", Annals New York Academy of Science, 199:pp. 265-273, 1972.
Reichl et al., "Effect of Arsenic on Cellular Metabolism after single or Repeated Injection in Guinea Pigs", Arch Toxicol., Suppl 13, p. 363-65, 1989.
Remington's Pharmaceutical Science, Mack Publishing Co., Easton, PA p. 1570-80, 1990.
Shibuya, "Studies on Experimental Arsenious Acid Positioning", Tokyo Jikeikai Ika Daigaku Zasshi, vol. 86, No. 4, p. 653, 1971.
Soignet et al., Complete Remission after Treatment of Acute Promyelocytic Leukemia with Arsenic Trioxide, J of Medicine, vol. 339, No. 19, Nov. 5, 1988.
Suehiro Shimotsuura et al., Studies on the Antineoplasmic Actions of $AS_2$-$O_3$, Shikwa Gakuho 86: 1237-1253, 1986.
Sun et al., "Ai Ling #1 and Traditional Chinese Medicine in the Treatment of 32 patients with Acute Promyelocytic Leukemia", Chinese J of Traditional Chinese and Western Medicine, vol. 12, No. 3, 1992.
Treleaven et al., "Arsenic and Ayurveda", Leukemia and Lymphoma, vol. 10, pp. 343-345, 1993.
USP Dictionary of USAN and International Drug Names, United States Pharmacopeia Conventions, Inc., Rockville, MD, p. 59, Nov. 1994.
Wang et al., "Arsenic and the Treatment of Leukemia", J Harbin Medical Univ., vol. 31, No. 5, Oct. 1997.
Zhang et al., "Traditional Chinese and Western Medicine in the Treatment of 27 patients with Malignant Lymphoma," Chinese J. Oncology, 10:61-62, 1988.
Zhang et al., Clinical Study on the Treatment of Acute Promyelocytic Leukemia with Ai Ling #1, J of Traditional Chinese and Western Medicine, vol. 4, No. 1, 1984, p. 19.
Zhang et al., Treatment of Acute Promyelocytic Leukemia with "713": Clinical Observations and Study of Action Mode on 117 Patients, J Harbin Medical University, vol. 29, No. 3, 1995.
Zhang et al., Treatment of Acute Promyelocytic Leukemia with Intravenous Arsenic Trioxide, Chinese J. of Hermatology, vol. 17, No. 2, 1996.

* cited by examiner

ARSENIC SULFIDE COMPOUNDS AND DERIVATIVES THEREOF FOR THE TREATMENT OF MALIGNANCIES

This is a continuation application of U.S. patent application Ser. No. 09/110,366, filed Jul. 6, 1998, which is herein incorporated by reference in its entirety.

1. FIELD OF INVENTION

The present invention relates to arsenic sulfide compounds. The present invention also relates to pharmaceutical compositions useful for treating cancer, preferably hematological cancer and more preferably leukemia or lymphoma, which comprise an arsenic sulfide compound. The present invention further relates to methods for treating cancer, preferably hematological cancer and more preferably leukemia or lymphoma, using an arsenic sulfide compound. Finally, the present invention relates to processes for producing arsenic disulfide ($As_4S_4$).

2. BACKGROUND OF THE INVENTION

2.1. Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia.

Leukemia refers to malignant neoplasms of the blood-forming tissues. Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL or AML) types. They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL or AML occurs at all ages and is the more common acute leukemia among adults; it is the form usually associated with irradiation as a causative agent.

One type of acute leukemias, acute promyelocytic leukemia (APL) is associated with the t(15;17) translocation, which generates a PML/RARα fusion protein between PML, a growth suppressor localized on nuclear matrix-associated bodies, and RARα, a nuclear receptor for retinoic acid (RA). PML/RARα was proposed to block myeloid differentiation through inhibition of nuclear receptor response, as does a dominant negative RARα mutant. In addition, in APL cells, PML/RARα displaces PML and other nuclear body (NB) antigens onto nuclear microspeckles, likely resulting in the loss of PML and/or NB functions. Diagnosis of acute promyelocytic leukemia (APL) is indicated most importantly on the morphological feature of APL cells in blood and bone marrow. A chromosomal translocation, t(15;17) is also typical of APL and is shown by banding or fluorescence in situ hybridization (FISH) staining techniques. The translocation can often be discovered in patients with APL, especially prior to complete remission. Polymerase chain reaction (PCR) of the patient's marrow also shows PML/RARα mRNA. Additionally, certain immunological markers, such as $CD33^+$, $CD13^+$, $CD9^+CD34^-$ and $HLA-DR^-$, are predominantly present in marrow cells.

Chronic leukemias are described as being lymphocytic (CLL) or myelocytic (CML). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of older persons. In CML (chronic myelocytic leukemia or chronic myeloid leukemia), the characteristic feature is the predominance of granulocytic cells of all stages of differentiation in blood, bone marrow, liver, spleen, and other organs. In the symptomatic patient at diagnosis the total WBC count is usually about 200,000/μL, but may reach 1,000,000/μL. CML is relatively easy to diagnose because of the presence of the Philadelphia chromosome.

With an incidence of 59,000 cases a year, the malignant lymphomas collectively represent the sixth most common causes of cancer in the United States. They are a heterogeneous group of disorders; about 15% of patients with malignant lymphomas have Hodgkin's disease, and the remainder have one of the non-Hodgkin's lymphomas. The etiology, epidemiology, pathology, clinical features, diagnostic evaluation and staging, treatment and management of lymphomas are disclosed in Malignant Lymphomas, the content of which is incorporated herein by reference. CML has been classified according to clinical courses such as, high grade, intermediate grade or low grade CML. Alternatively, CML has been classified according to immunological phenotyping such as T-cell, B-ell, or cytogenetic (chromosomal) aberrations. Histopathological changes and morphological changes are very important in the classification of CML. According to the current classification system, the non-Hodgkin's lymphomas are further subdivided into follicular, small cleaved cell and follicular, mixed small cleaved and large cell lymphoma, small lymphocytic lymphoma, mantle cell lymphoma, mucosa-associated lymphoid tissue lymphoma, monocytoid B cell lymphomas, follicular, large cell lymphoma, diffuse, small cleaved cell lymphoma, diffuse, mixed small cleaved and large cell lymphoma, diffuse, large cell lymphoma, immunoblastic lymphoma, thymic B cell lymphoma, diffuse, small noncleaved cell lymphoma, lymphoblastic lymphoma, peripheral T cell lymphoma, large cell anaplastic lymphoma and non-Hodgkin's lymphomas in acquired immunodeficiency syndrome.

The very nature of hematopoietic cancer necessitates using systemic chemotherapy as the primary treatment modality. Drugs selected according to sensitivities of specific leukemias and lymphomas are usually given in combination. Radiation therapy may be used as an adjunct to treat local accumulations of leukemic cells. Surgery is rarely indicated as a primary treatment modality, but may be used in managing some complications. Bone marrow transplantation from an HLA-matched sibling is sometimes indicated.

2.2. Arsenic and its Medical Uses

Arsenic has been considered to be both a poison and a drug for a long time in both Western and Chinese medical practices. In the latter part of the nineteenth century, arsenic was used frequently in attempts to treat diseases of the blood in the West. In 1878, it was reported that treatment of a leukemic patient with Fowler's solution (a solution containing potassium arsenite, valence +5) reduced markedly the count of white blood cells (Cutler and Bradford, *Am. J. Med. Sci., January* 1878, 81–84).

Further interests in the use of Fowler's solution as a palliative agent to treat chronic myelogenous leukemia (CML) was described by Forkner and Scott in 1931 (*J. Am. Med. Assoc.,* 1931, iii, 97), and later confirmed by Stephens and Lawrence in 1936 (*Ann. Intern. Med.* 9, 1488–1502). However, while the active chemical ingredient(s) of Fowler's solution was not determined, its toxicity was well recognized. Fowler's solution was administered strictly as an oral composition, and was given to leukemic patients as a solution until the level of white blood cells was depressed to an acceptable level or until toxicities (such as skin keratoses and hyperpigmentation) developed, while the patients enjoyed varying periods of remission. In the 1960's, Fowler's solution was still used occasionally in attempts to treat CML, however, most patients with CML were treated with other chemotherapeutic agents, such as busulfan, and/or radiation therapy (Monfardini et al., *Cancer,* 1973, 31:492–501). JP 51–88,620 discloses a process which involves crushing and oxidizing Fe, As and FeS, stirring in water, allowing to stand, and collecting the resulting supernatant containing ferrous, arsenic and sulphate ions, followed by filtration. JP 51–88,620 also discloses that the product of the above process can cure cancerous disease of stomach, duodenum, uterus, lung, pancreas etc.; and is effective in treating diabetes mellitus, heart disease, hypertension, asthma, neuralgia, rheumatism, etc.

Paradoxically, one of the long recognized effects of exposure to arsenic, whether the source is environmental or medicinal, is skin cancer (Hutchinson, 1888, *Trans. Path. Soc. Lond.,* 39:352; Neubauer, 1947, *Br. J. Cancer,* 1:192). There were even epidemiological data to suggest that the use of Fowler's solution over long periods could lead to an increased incidence of cancer at internal sites (Cuzick et al., *Br. J. Cancer,* 1982, 45:904–911; Kaspar et al., *J. Am. Med. Assoc.,* 1984, 252:3407–3408). The carcinogenicity of arsenic has since been demonstrated by the fact that it can induce chromosomal aberration, gene amplification, sister chromatid exchanges and cellular transformation (See e.g., Lee et al., 1988, *Science,* 241:79–81; and Germolec et al., *Toxicol. Applied Pharmacol.,* 1996, 141:308–318). In a mass screening for cancer in the realgar and tin mines, certain epidemical characteristics were found in precancerous lesion of lung cancer (Wang, *Chung Hua Chung Liu Tsa Chih,* 1989, 11(3):207–210). Pershagen and Bjorklund, *Cancer Lett.,* 1985, 27(1):99–104, showed that calcium arsenate is tumorigenic, while evidence is inconclusive for arsenic trisulfide (See also Yamamoto et al., *Int. J. Cancer,* 1987, 40(2):220–223). EPA/600/8-91/061 (OHEA-C-073-005) reports that arsenic and inorganic arsenic compounds, including, inter alia, arsenic disulfide and arsenic trisulfide, are human carcinogens. It further discloses that "since arsenic compounds are chemically convertible to the carcinogenic form(s) both in vitro and in vivo, and the exact species of inorganic arsenic that is directly carcinogenic in humans is not known, all the above inorganic arsenic compounds are of equal concern." Because of the known carcinogenic effect of arsenic, its only therapeutic use in human in Western medicine today is in the treatment of tropical diseases, such as African trypanosomiasis, (the organic arsenical, melarsoprol; See Goodman & Gilman's *The Pharmacological Basis of Therapeutics,* 9th edition, chapter 66, 1659–1662, 1997).

In traditional chinese medicine, arsenous acid or arsenic trioxide paste has been used to treat tooth marrow diseases, psoriasis, syphilis and rheumatosis (Chen et al., 1995, in *Manual of Clinical Drugs,* Shanghai, China, Shanghai Institute of Science and Technology, p. 830). In 1970's, arsenic trioxide had been applied experimentally to treat acute promyelocytic leukemia (APL) in China (commented by Mervis, 1996, *Science,* 273:578). The clinical efficacy of arsenic trioxide has recently been reinvestigated in 14 of 15 patients with refractory APL, where the use of an intravenous dose at 10 mg/day for 4–9 weeks was reported to result in complete morphologic remission without associated bone marrow suppression (Shen et al., 1997, *Blood,* 89:3354–3360). It was also shown that arsenic trioxide induced apoptosis (programmed cell death) in vitro in NB4 cells, an APL cell line, and that apoptosis was apparently associated with down-regulation of the oncogene bcl-2, and intracellular redistribution of the chimeric PML/RARα protein that are unique to APL cells (Chen et al., 1996, *Blood,* 88:1052–1061; Andre et al., 1996, *Exp. Cell Res.* 229: 253–260). It has been reported that the biological activity of arsenic is due to the ability of arsenic to direct the nucleoplasmic fraction of PML to nuclear bodies for degradation (Zhu et al., 1997, *Proc. Natl. Acad. Sci.,* 94:3978–3983).

Realgar (Xiong-Huang), an ore crystal containing mainly arsenic disulfide, has been popular in China for hundreds of years as a drug in traditional medicine and for keeping out the malign among laymen. CN 1,133,725 discloses that an exterior-use plaster which is prepared from 26 Chinese medicinal materials, including inter alia, realgar, can be used in treating liver cancer. CN 1,131,037 discloses that a new anti-carcinogen, suitable for curing exposure carcinosis, can be prepared from 21 Chinese medicinal materials, including inter alia, realgar. CN 1,122,700 discloses that a medicinal powder, comprising garcinia, realgar, frankincense, myrrh, artemisia, rupestris, rosin, vomiting nut and alum, can be used to treat mastosis, mammary tuberculosis sore and tumor. CN 1,119,113 discloses that a compound capsule comprising 24 Chinese medicinal materials, including inter alia, realgar, can be used in preventing and treating various cancers. CN 1,081,104 discloses that a plaster, which is produced from a variety of Chinese medicinal materials, including inter alia, red orpiment (a material similar to realgar), has long-term analgesic effect, especially for soothing cancer pain. CN 1,061,908 discloses that a composition produced from white arsenic, alum, realgar and myrrh can be used to treat cancer.

Although realgar has been used as one component to form a composition that has been indicted useful in treating or preventing various forms of cancer, realgar alone has never been suggested or used to treat cancer, especially leukemias or lymphomas. In addition, arsenic sulfide compound, whether alone or in combination, has never been suggested or used to treat any forms of cancer, including leukemias or lymphomas. On the contrary, there is concern in the medical field that realgar, or certain arsenic sulfide compounds, such as arsenic disulfide and arsenic trisulfide, are human carcinogens.

Qi and Bi, *Chung Yao Tung Pao,* 1983, 8(5):21 discloses a method of removing $As_2O_3$ from realgar ore using 1% HCl solution. Yuan et al., *Chung Yao Tung Pao,* 1988, 13(8):

17–21 discloses that treating realgar ore with HCl or vinegar can reduce $As_2O_3$ content in the realgar ore. Yuan et al., *Chung Yao Tung Pao*, 1988, 13(8):17–21 also discloses that besides $As_4S_4$ and $As_2O_3$, realgar contains more than 10 other trace elements, and since the efficacy of realgar depends on all those trace elements, it is a concern that washing realgar with HCl will remove most of the trace elements. Zhang et al., *Zhongguo Zhongyao Zaahi*, 1995, 20(9):537 discloses that treating realgar ore with yogurt (acidic milk) can reduce realgar's toxicity.

There is a great need for effective treatments of cancer, particularly hematological cancer including leukemias and lymphomas. Further, there is a great need for orally active anticancer agents. The present invention addresses these and other needs in the art.

3. SUMMARY OF THE INVENTION

Despite reports concerning the risks associated with the administration of arsenic sulfide compound to patients, applicant has discovered surprisingly that certain arsenic sulfide compounds have broad applicability in the treatment of various types of cancers, particularly, hematological cancer including leukemias and lymphomas. The arsenic sulfide compound can be used safely and effectively in mammals. Accordingly, the invention encompasses arsenic sulfide compounds, the preparation of these compounds, their incorporation into pharmaceutical compositions and their use to treat cancer.

The invention described herein encompasses any arsenic sulfide compound, or derivatives thereof, or a mixture with other arsenious compound, that can alleviate, reduce, ameliorate, or prevent cancer; or place or maintain in a state of remission of clinical symptoms or diagnostic markers associated with cancer, particularly hematological cancer including leukemias or lymphomas.

The present invention also encompasses pharmaceutical compositions useful for treating cancer, particularly hematological cancer including leukemia or lymphoma, which comprises an arsenic sulfide compound or realgar, preferably with a pharmaceutically acceptable carrier or excipient. In a preferred embodiment the invention encompasses a composition suitable for oral delivery, comprising one or more arsenic sulfide compounds and a pharmaceutically acceptable carrier or excipient in tablet, capsule, or other single unit dosage form. In another embodiment, the invention includes compositions suitable for topical, transdermal or parenteral delivery. Specific therapeutic regimens, pharmaceutical compositions, and kits are also provided by the invention.

The invention further encompasses a method of treating cancer, particularly hematoligical cancer including leukemia or lymphoma, comprising the administration of a therapeutically effective and non-lethal amount of an arsenic sulfide compound or realgar, preferably with a pharmaceutically acceptable carrier or excipient, to a human in need of such therapy.

The invention also encompasses the use of combination therapy to treat cancers, especially cancers which are refractory to other forms of treatment. In accordance with the present invention, arsenic sulfide compound can be used alone or in combination with other known therapeutic agents (including chemotherapeutics, radioprotectants and radiotherapeutics) or techniques to either improve the quality of life of the patient, or to treat cancer, particularly hematological cancer such as leukemia or lymphoma. The arsenic sulfide compounds can be used before, during or after the administration of one or more known chemotherapeutic agents. In addition, the arsenic sulfide compounds can be used before, during or after radiation treatment. The most preferred combinational therapy is an arsenic sulfide compound and arsenic trioxide used simultaneously or sequentially.

Finally, the invention encompasses a process for producing arsenic disulfide ($As_4S_4$) that is substantially free of arsenic trioxide ($As_2O_3$).

Particular compositions of the invention and their uses are described in the sections and subsections which follow.

5. DETAILED DESCRIPTION OF THE INVENTION

Compounds, compositions and methods for the treatment of cancer, particularly hematological cancer including leukemia and lymphoma, are described herein.

The present invention encompasses pharmaceutical compositions useful for treating cancer, particularly hematological cancer including leukemia or lymphoma, which comprises an arsenic sulfide compound or realgar, preferably with a pharmaceutically acceptable carrier or excipient. In a preferred embodiment the invention encompasses a composition suitable for oral delivery, comprising one or more arsenic sulfide compounds, and preferably a pharmaceutically acceptable excipient or carrier in tablet, capsule, or other single unit dosage form.

This invention also encompasses a method for treating cancer, particularly hematological cancer including leukemia or lymphoma, in a mammal including humans, which comprises administering to a subject in need of such therapy a therapeutically effective and non-lethal amount of one or more arsenic sulfide compounds, such as arsenic disulfide or arsenic trisulfide, preferably with a pharmaceutically acceptable carrier or excipient.

The invention further encompasses the use of combination therapy to treat cancers, especially cancers which are refractory to other forms of treatment. For treating leukemias or lymphomas, the most preferred combinational therapy is an arsenic sulfide compound and an arsenic trioxide used simultaneously or sequentially.

Finally, the invention encompasses a process for producing arsenic disulfide ($As_4S_4$) that is substantially free of arsenic trioxide ($As_2O_3$).

For clarity of disclosure, and not by way of limitation, the detailed description of the invention is divided into the subsections which follow.

5.1. The Arsenic Sulfide Compounds

As used herein, "arsenic sulfide compound" refers to, in a pharmaceutically acceptable form, a compound which comprises both arsenic and sulfur. The invention encompasses all pharmaceutically active species of arsenic sulfur, regardless whether such species are organic or inorganic molecules, salts or solution thereof, or mixtures thereof. The term "arsenic sulfide compound" also encompasses hydrated versions, such as aqueous solution, hydrolyzed products or ionized products, of these compounds; and these compound may contain different number of attached water molecules. Any arsenic sulfide compound(s), when used alone or in combination with other compounds, that can alleviate, reduce, ameliorate, prevent, or place or maintain in a state of remission of clinical symptoms or diagnostic markers associated with cancers, particularly hematological cancers including leukemias or lymphomas, can be used in the present invention.

Examples of "arsenic sulfide compound" include, but are not limited to, compounds with the molecular formulae of $(As_nS_m)_x$, wherein m, n and x are the same or different and alternate integrals. Examples of such compounds include, but are not limited to, arsenic disulfide ($As_4S_4$), arsenic pentasulfide ($As_2S_5$) and arsenic trisulfide ($As_2S_3$). In certain references, arsenic disulfide, arsenic sulfide or tetra arsenic tetra sulfide (TATS) are used interchangeably as the name of $As_4S_4$. For consistency, only "arsenic disulfide" will be used herein in the present application as the name of $As_4S_4$. Arsenic disulfide ($As_4S_4$) can be prepared from realgar according to procedures described in § 5.4. Alternatively, $As_4S_4$ can be prepared according to the procedures taught in *Gmelin's Arsenic* (8th Ed.) 17:417–422 (1952), or taught in *Schenk in Handbook of Preparative Inorganic Chemistry* 1:603 (G. Brauer, Ed., Academic press, New York, 2nd Ed. 1963). Arsenic pentasulfide ($As_2S_5$) can be prepared according to the procedures taught in *Schenk in Handbook of Preparative Inorganic Chemistry* 1:603 (G. Brauer, Ed., Academic press, New York, 2nd Ed. 1963). Arsenic trisulfide ($As_2S_3$) can be prepared according to the procedures taught in *Gmelin's Arsenic* (8th Ed.) 17:422–433 (1952).

5.2. Pharmaceutical Composition and Modes of Administration

The present invention provides a pharmaceutical composition useful for treating cancer, particularly hematological cancer including leukemia or lymphoma, in a mammal which comprises an effective amount of an arsenic sulfide compound, and preferably a pharmaceutically acceptable carrier or incipient. In a preferred embodiment the invention provides a composition suitable for oral delivery, comprising one or more arsenic sulfide compounds, and preferably a pharmaceutically acceptable carrier or incipient in tablet, capsule, or other single unit dosage form.

In a specific embodiment, the arsenic sulfide compound is selected from the group consisting of $As_2S_2$, $As_2S_3$, $As_2S_5$ and $As_4S_4$. Preferably, the arsenic sulfide compound is $As_4S_4$. More preferably, the $As_4S_4$ is produced according to the methods disclosed in § 5.4. Mixtures of these compounds can also be used.

In another specific embodiment, the amount of the arsenic sulfide compound, e.g., $As_4S_4$, is from about 100 mg to about 2 g per unit dosage form.

In still another specific embodiment, the pharmaceutically acceptable carrier is a plant semen. Preferably, the plant semen is seman platycladi.

In yet another specific embodiment, the arsenic sulfide compound is present in an amount on weight basis, relative to the pharmaceutically acceptable carrier, in about equal proportions. Preferably, the arsenic sulfide compound is $As_4S_4$ and the pharmaceutically acceptable carrier is seman platycladi.

The present invention also provides a pharmaceutical composition useful for treating cancer, particularly hematological cancer including leukemia or lymphoma, in a mammal which comprises an effective amount of an arsenic sulfide compound, preferably with a pharmaceutically acceptable carrier or incipient, and further comprising an effective amount of an arsenious compound, wherein the arsenic sulfide compound and the arsenious compound are not the same compound. In a specific embodiment, the arsenious compound is selected from the group consisting of $As_2S_2$, $As_2S_3$, $As_2S_5$, $As_4S_4$ and $As_2O_3$. Preferably, the arsenic sulfide compound is $As_4S_4$.

Although § 5.4. discloses a process for producing $As_4S_4$, which is substantially free of $As_2O_3$, these two compounds can be used in combination. In fact, in one of the preferred embodiment, the present invention provides a pharmaceutical composition useful for treating cancer, particularly hematological cancer including leukemia or lymphoma, in a human which comprises an effective amount of $As_4S_4$, $As_2O_3$ and a pharmaceutically acceptable carrier; or in a method of treatment which employs both $As_4S_4$ and $As_2O_3$.

The present invention further provides a pharmaceutical composition useful for treating caner, particularly hematological cancer including leukemia or lymphoma, in a human which comprises an effective amount of an arsenic sulfide compound, and preferably a pharmaceutically acceptable carrier or incipient, and further comprising an effective amount of a therapeutic agent including but is not limited to mustard compounds, nitrogen mustard, chlorambucil, melphalan, cyclophosphamide, busulfan, 6-mercaptopurine, 6-thioguanine, cytarabine, cytosine arabinoside, 5-fluorouracil, floxuridine, methotrexate, vincristine, vinblastine, taxol, etoposide, temiposide, dactinomycin, daunorubicin, doxorubicin, epirubicin, mitoxantron, bleomycin, mitomycin, cisplatin, carboplatin, estramustine phosphate, hydroxyurea, BCNU, procarbazine, VM-26 (vumon), interferons and all-trans retinoic acid.

The present invention provides pharmaceutical composition useful for treating cancer, particularly hematological cancer including leukemia or lymphoma, in a human which comprises an effective amount of realgar and a pharmaceutically acceptable carrier or incipient.

According to the present invention, the arsenic sulfide compounds and their physiologically acceptable salts or solvates may be formulated for oral or parenteral administration.

For oral administration, the pharmaceutical preparation may also be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free wateror other solvents, before use.

The invention also provides kits for carrying out the therapeutic regimens of the invention. Such kits comprise in one or more containers therapeutically effective amounts of the arsenic sulfide compounds in pharmaceutically acceptable form. The arsenic sulfide compound in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of arsenic sulfide compounds by a clinician or by the patient.

The magnitude of a therapeutic dose of an arsenic compound in the acute or chronic management of cancer, including leukemia or lymphoma, will vary with the severity of the condition to be treated and the route of administration. The dose, and perhaps dose frequency, will also vary according to the age, body weight, condition and response of the individual patient. For example, the total daily dose ranges of arsenic disulfide for the conditions described herein are generally from about 100 mg to about 2 g administered in divided doses administered parenterally or orally or topically.

Desirable blood levels may be maintained by a continuous infusion of an arsenic sulfide compound as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

Again, any suitable route of administration may be employed for providing the patient with an effective dosage of an arsenic sulfide compound. For example, oral, transdermal, iontophoretic, parenteral (subcutaneous, intramuscular, intrathecal and the like) may be employed. Dosage forms include tablets, troches, cachet, dispersions, suspensions, solutions, capsules, patches, and the like. (See, *Remington's Pharmaceutical Sciences*).

In practical use, an arsenic sulfide compound can be combined as the active ingredient in intimate admixture with a pharmaceutical carrier or incipient according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives, liposomes and the like know to those skilled in the art. Examples of such parenteral compositions include, but are not limited to Dextrose 5% w/v, normal saline or other solutions. The total dose of the arsenic sulfide compound may be administered in a vial of intravenous fluid, e.g., ranging from about 2 ml to about 2000 ml. The volume of dilution fluid will vary according to the total dose administered.

5.3. Methods of Treatment

The term "a method for treating cancer" as used herein means that the disease and the symptoms associated with the cancer are alleviated, reduced, ameliorated, prevented, placed in a state of remission, or maintained in a state of remission. For example, where the cancer to be treated is leukemia, the methods of treatment of the invention can lower the white blood cell count, or reduce lymphocytosis in a human under treatment.

In one embodiment, the present invention provides a method for treating cancer, particularly hematological cancer including leukemia or lymphoma, in a mammal comprising administering to said mammal, to which such treatment is needed, an effective amount of an arsenic sulfide compound and preferably a pharmaceutically acceptable carrier or incipient.

In another embodiment, the present invention provides a method for treating cancer, particularly hematological cancer including leukemia or lymphoma, in a mammal comprising administering to said mammal, to which such treatment is needed, an effective amount of an arsenic sulfide compound, an arsenious compound, and preferably a pharmaceutically acceptable carrier or incipient, wherein the arsenic sulfide compound and the arsenious compound are not the same compound.

In still another embodiment, the present invention provides a method for treating cancer, particularly hematological cancer including leukemia or lymphoma, in a human comprising administering to said human, to which such treatment is needed, an effective amount of the pharmaceutical compositions disclosed in § 5.2.

Examples of hematological cancer that can be treated by the present methods include, but are not limited to, acute lymphoblastic leukemia (ALL), acute lymphoblastic B-cell leukemia, acute lymphoblastic T-cell leukemia, acute non-lymphoblastic leukemia (ANLL), acute myeloblastic leukemia (AML), acute promyelocytic leukemia (APL), acute monoblastic leukemia, acute erythroleukemic leukemia, acute megakaryoblastic leukemia, chronic myelocytic leukemia (CML), chronic lymphocytic leukemia (CLL), multiple myeloma, myelodysplastic syndrome (MDS) such as refractory anemia with excessive blast (RAEB) and RAEB in transformation to leukemia (RAEB-T), and chronic myelo-monocytic leukemia (CMML). Preferably, the hematological cancer to be treated is acute promyelocytic leukemia (APL), chronic myelocytic leukemia (CML), chronic lymphocytic leukemia (CLL) and multiple myeloma.

Examples of lymphoma that can be treated by the present methods include, but are not limited to, high grade lymphoma, intermediate grade lymphoma and low grade lymphoma. Preferably, the lymphoma to be treated is non-Hodgkin's lymphoma.

The skilled artisan will recognize that other cancers, particularly hematological cancers, may be treated in accordance with the present invention.

In a specific embodiment, the arsenic sulfide compound is selected from the group consisting of $As_2S_2$, $As_2S_3$, $As_2S_5$ and $As_4S_4$. Preferably, the arsenic sulfide compound is $As_4S_4$. More preferably, $As_4S_4$ is produced according to the methods disclosed in § 5.4. In another specific embodiment, the arsenious compound is selected from the group consisting of $As_2S_2$, $As_2S_3$, $As_2S_5$, $As_4S_4$ and $As_2O_3$. In a method wherein the arsenic sulfide compound being used is $As_4S_4$, the arsenious compound, preferably, is $As_2O_3$.

The present invention also provides a method for treating a human who is newly diagnosed of, or who is in relapsing stage of leukemia or lymphoma, preferably, acute promyelocytic leukemia (APL), chronic myelocytic leukemia (CML), non-Hodgkin's lymphoma, chronic lymphocytic leukemia (CLL) or multiple myeloma, which comprises: a) administering to said human an effective amount of an arsenic sulfide compound a number of times for a first period of time; and b) administering to said human an effective amount of an arsenic sulfide compound a reduced number of times for a second period of time, wherein the sum of the first period and second period does not exceed 100 days. In one specific embodiment, the arsenic sulfide compound, e.g., $As_4S_4$, is administered 4 times daily for the first period of time. In another specific embodiment, the arsenic sulfide compound, e.g., $As_4S_4$, is administered 3–4 times daily for the second period of time.

The present invention further provides a method for maintaining a human in complete remission stage of leukemia, preferably, acute promyelocytic leukemia (APL), chronic myelocytic leukemia (CML), non-Hodgkin's lymphoma, chronic lymphocytic leukemia (CLL) or multiple myeloma, which comprises: a) administering to a human who is in remission stage of said leukemia or lymphoma an effective amount of an arsenic sulfide compound for a first period of time; b) conducting clinical tests on said human for said leukemia or lymphoma; and c) administering to said patient an effective amount of an arsenic sulfide compound, if results of the clinical tests in step (b) indicate that the administration is necessary to completely maintain the patient in remission stage of said leukemia or lymphoma. In one specific embodiment, the arsenic sulfide compound, e.g., $As_4S_4$, is administered 3–4 times daily for the first period of time. In another specific embodiment, the second period of time ranges from about 2 weeks to about years.

As used herein, "complete remission" is defined as having less than 5% blast cells and leukemic promyelocytes with normal blood pictures accompanied by no clinical manifestations of leukemia. Clinical and other tests for APL include, but are not limited to, the morphological feature of APL cells in blood and bone marrow, a chromosomal translocation, e.g., t(15;17), existence of PML/RARα mRNA and other immunological markers that are indicative of APL.

In accordance with the present invention, arsenic sulfide compounds can be used alone or in combination with other known therapeutic agents (including chemotherapeutics, radioprotectants and radiotherapeutics) or techniques to either improve the quality of life of the patient, or to treat leukemia or lymphoma. For example, the arsenic sulfide compounds can be used before, during or after the administration of one or more known antitumor agents including but not limited to mustard compounds, nitrogen mustard, chlorambucil, melphalan, cyclophosphamide, busulfan, 6-mercaptopurine, 6-thioguanine, cytarabine, cytosine arabinoside, 5-fluorouracil, floxuridine, methotrexate, vincristine, vinblastine, taxol, etoposide, temiposide, dactinomycin, daunorubicin, doxorubicin, epirubicin, mitoxantron, bleomycin, mitomycin, cisplatin, carboplatin, estramustine phosphate, hydroxyurea, BCNU, procarbazine, VM-26 (vumon), interferons and all-trans retinoic acid (ATRA), (See, for example, the *Physician Desk References* 1997). In addition, the arsenic sulfide compounds can be used before, during or after radiation treatment.

As used herein the terms "a therapeutic agent", "therapeutic regimen", "radioprotectant", "chemotherapeutic" mean conventional drugs and drug therapies, including vaccines, for treating cancer, viral infections, and other malignancies, which are known to those skilled in the art. "Radiotherapeutic" agents are well known in the art.

In a preferred embodiment, the arsenic sulfide compound of the invention is administered orally before, during or after a patient undergoes other types of chemotherapy or radiotherapy.

5.4. Processes for Producing Arsenic Disulfide

The present invention provides a process for producing arsenic disulfide ($As_4S_4$), said $As_4S_4$ being substantially free of arsenic trioxide ($As_2O_3$), which comprises: (a) suspending realgar in an aqueous solution at pH about 6–7; (b) adjusting pH of the realgar suspension to pH about 4–4.5; (c) decanting resultant supernatant and resuspending the remaining sediment in a solution at pH about 4–4.5; (d) repeating step (c) until arsenic concentration in said supernatant is less than 20 mg/L; (e) washing the remaining sediment from step (d) with an aqueous solution at pH about 6–7; and (f) drying said powder under non-oxidizing condition.

As used herein, "substantially free of arsenic trioxide ($As_2O_3$)" means that the content of $As_2O_3$, on weight basis, is less than 0.15% in the produced $As_4S_4$. Preferably, the content of $As_2O_3$ is less than 0.1%.

Realgar exists widely in the nature. For instances, realgar has been found in Sb ores of Yugoslavia, in hot spring deposits in the former USSR, in borate deposits in Turkey, and in gold ores of Montana and Armenia (*Dictionary of Inorganic Compounds* (Ed. Macintyre et al., Chapman & Hall 1992) Vol. 1, p119). Realgar that exists naturally can be used as the raw material for producing $As_4S_4$ in the present method.

In a specific embodiment, the aqueous solution that is used to suspend mined realgar and to wash the realgar sediment in steps (a) and (e) is deionized double distilled water.

In another specific embodiment, the acidic solution that is used to adjusting pH and resuspending the realgar sediment in steps (b) and (c) is hydrochloric acid or acetic acid solution. HCl and HAc can be used interchangeably during the process. Preferably, 0.1 M HCl solution or 0.1 M HAc solution is used.

The arsenic disulfide powder can be dried under non-oxidizing condition by the methods known in th art. Preferably, the arsenic disulfide powder is dried at low temperature.

The present invention also provides arsenic disulfide that is produced according to the above processes.

6. EXAMPLES

6.1 Producing Arsenic Disulfide Substantially Free of Arsenic Trioxide

Realgar crystals were carefully, manually selected from mixed material sources by experienced personnel. Usually, only a very small amount of purified product can be produced from a large amount of unpurified realgar, which contains stones and toxic substances such as $As_2O_3$, $(CaMg)_3 (AsO_3)$ and $(CaMg)(AsO_4)_2$. In this example, the realgar ore contains >98% of $As_4S_4$. The remaining of the realgar ore contains water and other impurities.

Stones were removed from the realgar ore. The resulting realgar crystal, weighed 50–100 g, was placed in a large mortal filled with 0.5 liter of deionized double-distilled water (DD water). The crystal was broken up, ground with a pestle and suspended in DD water. The pH of the suspension was adjusted to pH 4.5 by adding 0.12 M HCl. This grinding process continued for 2 hours either manually or in a mortal with motorized pestle. The sediment was allowed to settle, and the supernatant being left was decanted or siphoned. The above washing and grinding process was repeated three times, each for 2 hours, with HCl solution (pH 4.5). The fourth process was done in a big beaker with a magnetic stirrer overnight. The supernatant was decanted and tested for arsenic with atomic absorption spectrophotometer. Arsenic in the supernatant should not exceed 20 mg/L. Otherwise, the above washing process with the magnetic stirrer in the beaker should be continued for additional 3–4 hours until arsenic concentration in the supernatant was below 20 mg/L. The supernatant was discarded. The remaining arsenic disulfide sediment was washed with 1 liter DD water twice, each for two hours in a beaker with magnetic stirring. The remaining fine powder was dried at 4° C.

6.2 Producing Arsenic Disulfide Formulation

*Seman platycladi*, a plant semen, was used as a pharmaceutical carrier in formulating a arsenic-disulfide-containing composition that is suitable for oral administration. *Seman platycladi* was obtained from herb medicine market. 0.5 g of $As_4S_4$, produced by the aforementioned method, was mixed and ground with 0.25 g of *seman platycladi*. The mixture was then placed into capsules resulting a total weight of 0.5 g per capsule. Such capsule is particularly useful in oral administration.

In other experiments, a number of solvents, such as polyvinylpyrrolidone, pyrrolidone, alcohol, ether, di-sodium hydrophosphate, mercaptopurine and sodium bicarbonate, were tested to increase solubility of $As_4S_4$. $As_4S_4$ was shown to be soluble at various concentrations of the above solvents. Accordingly, $As4S_4$ solubilized in the above solvents is useful for intravenous administration.

6.3 Clinical Treatments

6.3.1 Treatment Protocols

Newly diagnosed, or relapsing patients are given a different protocol of treatment than are those patients who are in current remission. To induce complete remission, the patient is administered a measured dose of the arsenic disulfide-containing compound four times daily for three days. Preferably the dose given will range from approximately 0.5 to approximately 0.75 gram of arsenic disulfide. This equates to 2 to 3 capsules, according to the above formulation, by mouth for one dose. After the initial three days, the patient is given the compound three times daily until remission is induced. To prevent complications due to the potential build up of arsenic in the body, treatment should not exceed 100 days. In most cases, favorable response should be induced before forty days of treatment. These later doses may be somewhat reduced in amount compared to the original three day dosages. If after 100 days of treatment the patient does not respond favorably, the treatment should be stopped. At this point, the patient should be reevaluated through testing, and allowed to rest before beginning another course of treatment according to the present protocol.

The protocol for maintaining patients in complete remission, or treating those in remission with residual genetic markers of leukemia differ from those outlined above. To maintain complete remission, the patient is given a measured amount, to be adjusted according to test results, of the compound containing arsenic disulfide three to four times daily for fourteen days. The patient then abstains from treatment for a set period of time. During this time, the patient is tested. Treatment is adjusted according to test results with the period of abstention lasting from two weeks to 100 days, depending upon results. The length of the maintenance procedure varies according to patients' conditions, and may last as long as 3 years (including treating and resting periods). Each dose during this phase of treatment preferably contains arsenic disulfide in the range of approximately 0.50 to 0.75 gram. Once again the preferred method of administration is orally through use of a capsule as described above. Usually, a maintenance treatment is divided into two stages.

6.3.2 Case Studies

All patients who make up a part of the case studies have been diagnosed with APL on the basis of cell morphology of AML-M3, that is acute hypergranular promyelocytic leukemia, immunological cell markers, chromosomal analysis showing (15;17) translocation, and positive PML/RARα mRNA expression. Some patients were referred to the study with a diagnosis based solely on pathologic changes in cell morphology; these patients' diagnoses were tracked and reconfirmed throughout the study. Chronic myeloid leukemia and lymphoma patients have also benefitted from arsenic disulfide treatment, as illustrated by case studies 3 and 4.

Inclusion criteria for the study included patients in APL relapse, patients who are unable to attain complete remission with ATRA or cytotoxic agents, patients in complete remission after conventional treatment who show residual leukemic cells with PCR analysis, indicating likelihood of relapse. Fifty-one patients met the inclusion criteria for the study.

Exclusion criteria for the study included history of hypersensitivity to arsenic compounds, previous treatment with arsenic-containing medications, patient in critical condition, excessively low or high white blood counts, existing heart, liver or kidney conditions, and severe infection. Three patients were excluded on these grounds, leaving 48 patients in the study. All 48 cases were treated with arsenic disulfide according to the above protocol. ATRA or other cytotoxic agents were not used. All 48 patients are living and Leukemia free as of April, 1998.

Ten of these patients were either newly diagnosed or in relapse (i.e. not in remission) before treatment according to the present protocol. Eight of these patients were given one course of treatment before attaining complete remission, the remaining two patients took two and three courses of treatment each. All ten patients are alive and remain in complete remission, leukemia free.

Many patients in this study in complete remission before treatment showed positive results for markers indicating residual leukemia cells. After treatment according to the maintenance protocol outlined above, all such patients turned out to be persistently negative when tested.

Side effects of treatment with arsenic disulfide are minimal when compared to those of other antineoplastic agents. Potential side effects include loss of appetite, mild diarrhea, and transient reversible increase of aspartate aminotransferase (AST). A minority of patients experienced cutaneous itching or puffing of the eyelids, and mild leukopenia occurred slowly in 34% of patients. One patient had thrombocytopenia without bleeding. There were no deaths associated with the use of arsenic sulfide.

Case Study 1

Figure 1:
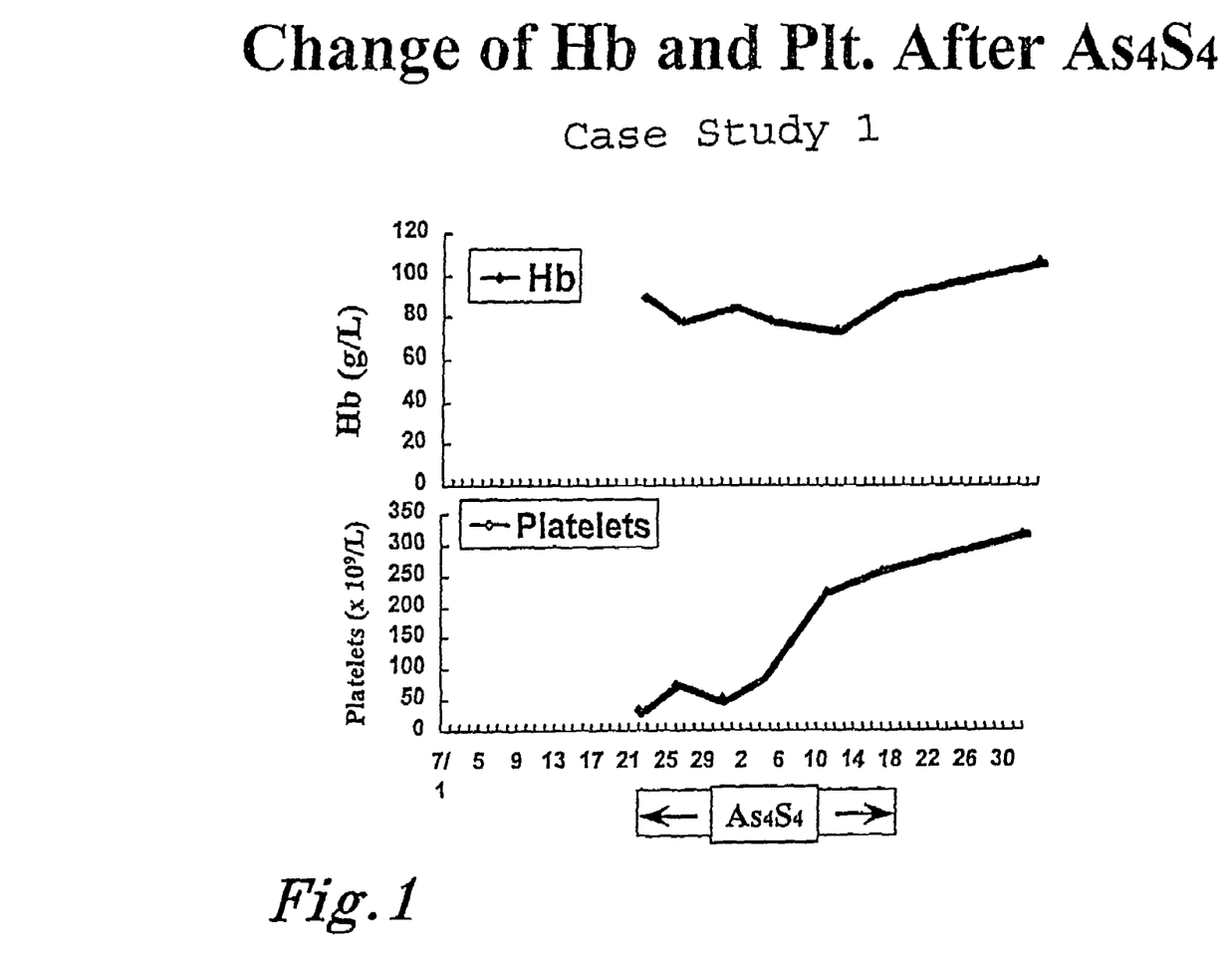
FIG. 1 is a graph showing change of hemoglobin and platelet counts for case study 1 (treatment of a newly-diagnosed APL patient using arsenic disulfide).
Figure 2:
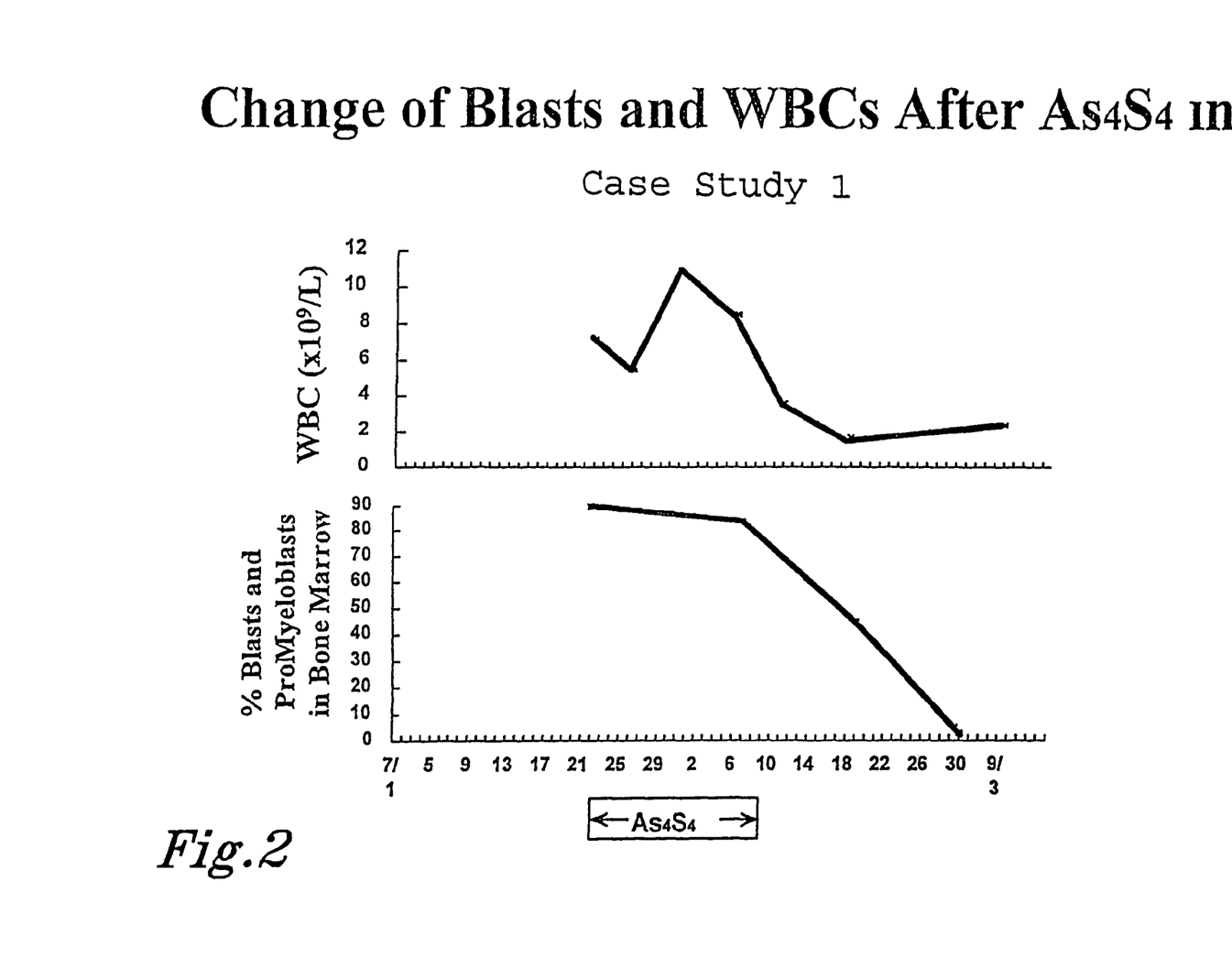
FIG. 2 is a graph showing change of blast and white blood cell counts for case study 1 (treatment of a newly-diagnosed APL patient using arsenic disulfide).

A 35 year old male was diagnosed with APL on Jul. 22, 1997, after noticing onset of symptoms the previous June. The patient had white blood cell counts of $7.04 \times 10^9$/L, hemoglobin 9 gm %, and platelet levels at $34.0 \times 10^9$/L. Cytogenetic analysis showed the (15;17) translocation, and PCR showed PML-RARα(+). One day of ATRA treatment was given to the patient prior to beginning arsenic disulfide treatment. The treatment per the above protocol began on Jul. 22, 1997. Treatment was discontinued on Aug. 19, 1997 after twenty-five days of treatment. On Aug. 28, 1997, tests revealed the patient was in complete remission, having blast cells and leukemic promyelocytes less than 5%. This level was reached after only 36 days of treatment according to the protocol. As shown in FIG. 1, the patient saw a marked increase in hemoglobin and platelet levels. FIG. 2 shows the dramatic decrease in blasts and white blood cells after the arsenic disulfide treatment was used.

Case Study 2

Figure 3:
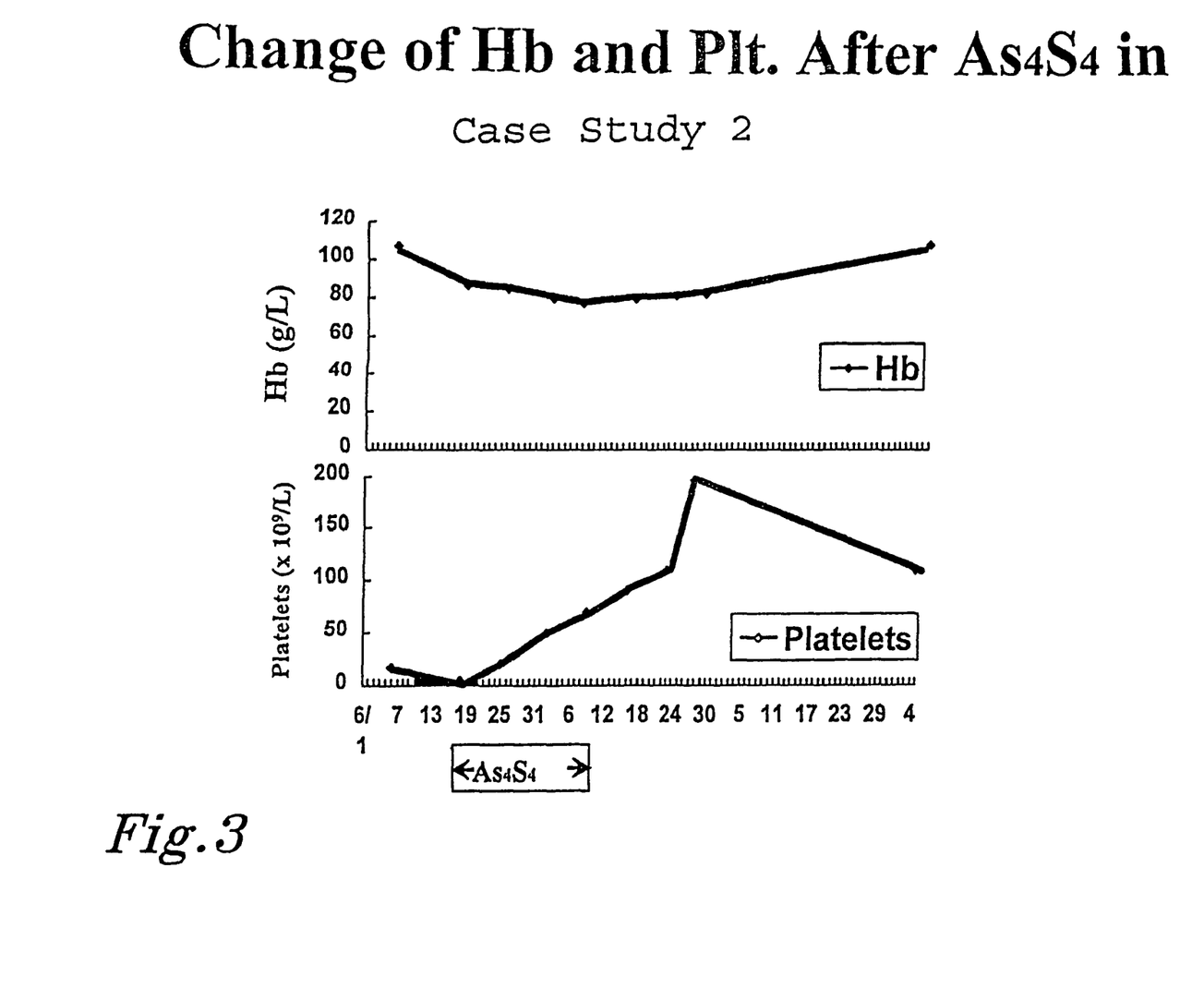
FIG. 3 is a graph showing change of hemoglobin and platelet counts for case study 2; (treatment of an APL patient in relapsing stage using arsenic disulfide).
Figure 4:
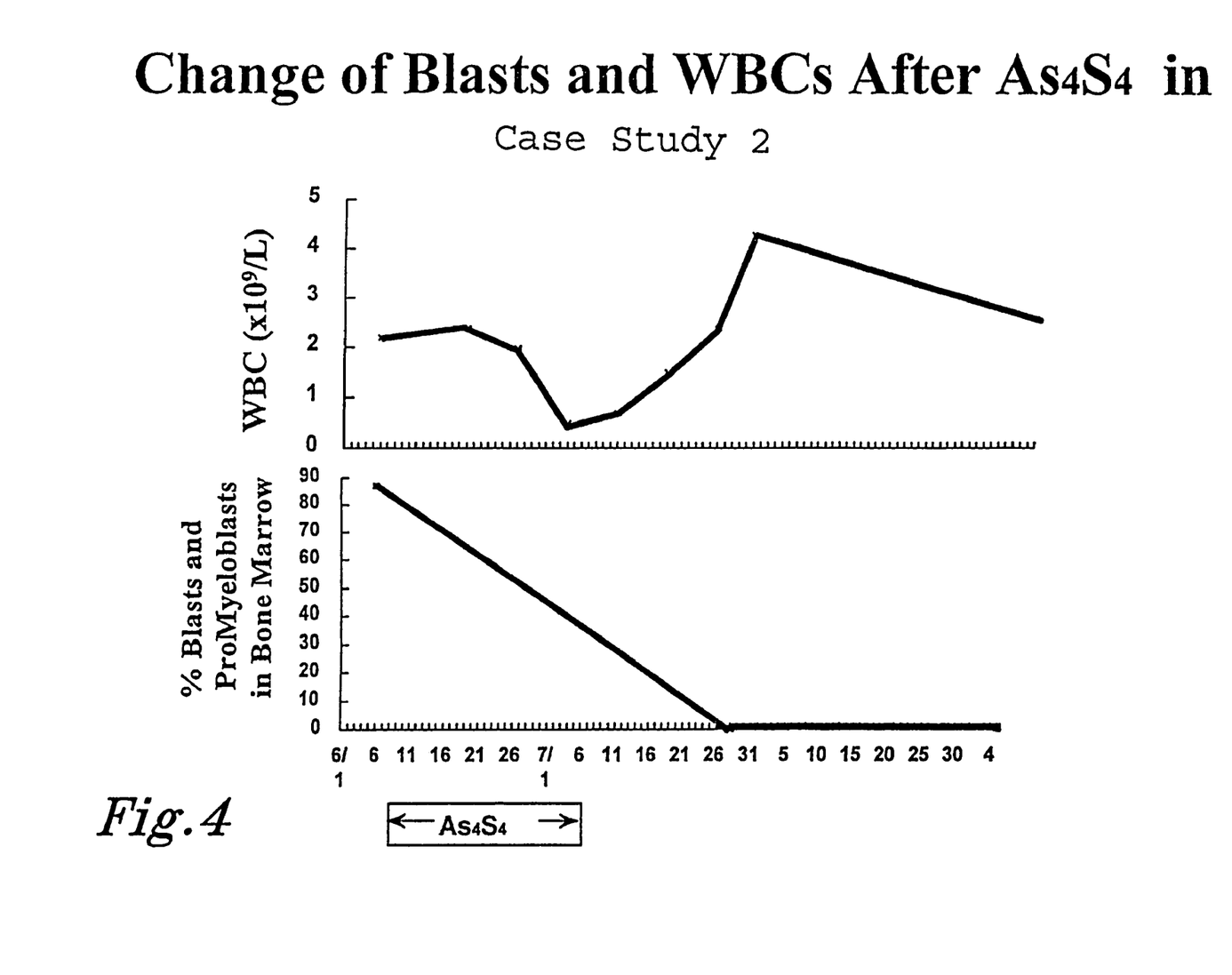
FIG. 4 is a graph showing change of blast and white blood cell counts for case study 2 (treatment of an APL patient in relapsing stage using arsenic disulfide).

A 32 year old female was diagnosed with APL on May 24, 1996. She was treated for 40 days with ATRA, and subsequently Harringtonin/Ara-C in four courses. The patient met some success, and had a rest period of six months. Patient relapsed on Jun. 6, 1997. Her white blood cell count was $2.2 \times 10^9$/L, hemoglobin 10.7 gm %, and platelet count $1.5 \times 10^9$/L. Treatment with arsenic disulfide began on Jul. 9, 1997. The patient was treated according to protocol for 21 days. The patient went into complete remission on Jul. 28, 1997. FIG. 3 shows that the patient saw a change in hemoglobin and platelet levels. FIG. 4 shows the dramatic change in blasts and white blood cells after the arsenic disulfide treatment was used.

Case Study 3

A 40 year old male was diagnosed as having chronic myeloid leukemia (CML) in February, 1959. At that time, he had a white blood cell count of $1.5 \times 10^5$/mm$^3$ and a platelet level of $1.4 \times 10^5$/mm$^3$. Initially, he was treated with Myleran. On Jan. 20, 1960, the white blood cell count was $3.15 \times 10^6$/mm$^3$ showing a differential count of 11% promyelocyte and myelocyte. The bone marrow picture showed increased cellularity with a preponderance of myeloid series with 21% of myelocytes. Patient was given 0.6 gram of arsenic disulfide twice daily. While being treated, blood and bone marrow pictures were controlled. The patient died, on Sep. 5, 1965 from infection unrelated to the arsenic sulfide treatment.

Case Study 4

A 15 year old female diagnosed with non-Hodgkin's lymphoma in September 1996 was treated with a combination chemotherapy regimen and had cranial irradiation for meningeal lymphoma. She also had high dose chemo-radiotherapy for autologous stem cell transplant. The patient has several relapses including intracranial relapse and a large amount of lymphoma cells in peripheral blood with typical clinical and laboratory features of lymphoma/leukemia. She became resistant to conventional anticancer treatment. In March, 1998 she received arsenic disulfide treatment according to protocol. Since that time, she has been in remission.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A pharmaceutical composition useful for treating a hematological cancer in a mammal, consisting of (A) at least one arsenic sulfide compound, (B) a pharmaceutically acceptable carrier or excipient, and optionally (C) an effective amount of a therapeutic agent selected from the group consisting of mustard compounds, nitrogen mustard, chliorambucil, melphalan, cyclophosphamide busulfan, 6-mercaptopurine, 6-thioguanine, cytarabine, cytosine arabinoside, 5-fluorouracil, floxuridine, methotrexate, vincristine, vinblastine, taxol, etoposide, temiposide, dactinomycin, daunorubicin, doxorubicin, epirubicin, mitoxantron, bleomycin, mitomycin, cisplatin carboplatin, estramustine phosphate, hydroxyurea, BCNU, procarbazine, VM-26 (vumon), interferons and all-trans retinoic acid.

2. The pharmaceutical composition of claim 1, wherein said mammal is a human.

3. The pharmaceutical composition of claim 1, wherein the arsenic sulfide compound is selected from the group consisting of $As_2S_2$, $As_2S_3$, $As_2S_5$ and $As_4S_4$.

4. The pharmaceutical composition of claim 3, wherein the arsenic sulfide compound is $As_4S_4$.

5. The pharmaceutical composition of claim 1, wherein the amount of said arsenic sulfide compound is from about 100 mg to about 2 g.

6. The pharmaceutical composition of claim 1, wherein the pharmaceutically acceptable carrier or excipient is a plant semen.

7. The pharmaceutical composition of claim 1, wherein the plant semen is *Seman platycladi*.

8. The composition of claim 1, wherein the hematological cancer is selected from the group consisting of acute lymphoblastic leukemia, acute lymphoblastic B-cell leukemia, acute lymphoblastic T-cell leukemia, acute nonlymphoblastic leukemia, acute myeloblastic leukemia, acute promyelocytic leukemia, acute monoblastic leukemia, acute erythroleukemic leukemia, acute megakaryoblastic leukemia, chronic myelocytic leukemia, myelodysplastic syndrome, refractory anemia with excessive blast (RAEB) and RAEB in transformation to leukemia (RAEB-T), and chronic myelo-monocytic leukemia.

9. The composition of claim 1, wherein the pharmaceutical composition is formulated for oral delivery to a human.

* * * * *